(12) United States Patent
Sewell

(10) Patent No.: US 8,859,579 B2
(45) Date of Patent: Oct. 14, 2014

(54) COMPOSTIONS AND METHODS FOR PREVENTING AND/OR TREATING DISORDERS ASSOCIATED WITH CEPHALIC PAIN

(76) Inventor: Richard Andrew Sewell, New Haven, CT (US)

(*) Notice: Subject to any disclaimer, the term of this patent is extended or adjusted under 35 U.S.C. 154(b) by 740 days.

(21) Appl. No.: 12/408,438

(22) Filed: Mar. 20, 2009

(65) Prior Publication Data

US 2009/0264456 A1    Oct. 22, 2009

Related U.S. Application Data

(60) Provisional application No. 61/038,537, filed on Mar. 21, 2008.

(51) Int. Cl.
*A61K 31/44* (2006.01)
*C07D 457/00* (2006.01)

(52) U.S. Cl.
USPC .............................. 514/288; 514/279; 546/69

(58) Field of Classification Search
None
See application file for complete search history.

(56) References Cited

U.S. PATENT DOCUMENTS

| | | | | |
|---|---|---|---|---|
| 3,228,959 | A * | 1/1966 | Gyermek | 548/504 |
| 4,808,588 | A * | 2/1989 | King | 514/213.01 |
| 8,415,371 | B2 * | 4/2013 | Halpern et al. | 514/279 |

FOREIGN PATENT DOCUMENTS

| WO | WO 2004112723 A2 * | 12/2004 |
|---|---|---|
| WO | 2010/033392 | 3/2010 |

OTHER PUBLICATIONS

Frood, "Cluster busters," Nature Medicine, vol. 13, No. 1, Jan. 2007, pp. 10-11.*
May, "Cluster headache: pathogenesis, diagnosis, management," The Lancet, vol. 366, pp. 843-855, Sep. 2005).*
Friedman et al., "Headache. Pharmacological approach to treatment," Calif. Med., 95:145-149 (1961).
Frood, "Cluster Busters," Nat. Med., 13(1):10-11 (2007).
Halpern et al., "Hallucinogenic botanicals of America: a growing need for focused drug education and research," Life Sci., 78(5):519-526 (2005).
Halpern et al., "Hallucinogens and dissociative agents naturally growing in the United States," Pharmacol. Ther., 102 (2):131-138 (2004).
Karst et al., "The non-hallucinogen 2-bromo-lysergic acid diethylamide as preventative treatment for cluster headache: an open, non-randomized case series," Cephalalgia, 30(9):1140-1144 (2010).
Kimball et al., "Effect of serotonin in migraine patients," Neurology, 10:107-111 (1960).
Miller et al., "Isolation and Identification of Lysergic Acid Amide and Isolysergic Acid Amide as the Principal Ergoline Alkaloids in *Argyreia nervosa*, a Tropical Wood Rose," Journal of the AOAC, 53(1):123-127 (1970).
Sewell et al., "Response of cluster headache to psilocybin and LSD," Neurology, 66(12):1920-1922 (2006).
Sicuteri, "Hypothesis: migraine, a central biochemical dysnociception," Headache, 16(4):145-159 (1976).
Sicuteri, "Mast cells and their substance: their role in the pathogenesis of migraine," Headache, 3:86-92 (1963).
Sicuteri, "Prophylactic treatment of migraine by means of lysergic acid derivatives," Triangle, 67:116-125 (1963) (in German) and English translation.
Sicuteri, "Treatment Specificity of Hallucinogenic and Non-Hallucinogenic Derivatives in Vascular Headaches," Records from the international workings on selective psycho-stimulant drugs 1-8 (1963) (in Italian) and English translation.

* cited by examiner

*Primary Examiner* — Sreeni Padmanabhan
*Assistant Examiner* — Jody Karol
(74) *Attorney, Agent, or Firm* — McAndrews, Held & Malloy Ltd.

(57) ABSTRACT

Compounds, e.g., of formula (I) and (Ia), pharmaceutical compositions comprising the compounds and methods of using the compounds and pharmaceutical compositions for treating pain disorders, e.g., disorders associated with cephalic pain, are provided.

11 Claims, No Drawings

COMPOSTIONS AND METHODS FOR PREVENTING AND/OR TREATING DISORDERS ASSOCIATED WITH CEPHALIC PAIN

This application claims priority from 61/038,537, filed Mar. 21, 2008, hereby incorporated by reference in its entirety.

FIELD OF THE INVENTION

Compounds, pharmaceutical compositions comprising the compounds and methods of using the compounds and pharmaceutical compositions for treating pain disorders, e.g., disorders associated with cephalic pain, are provided.

BACKGROUND OF THE INVENTION

Disorders associated with cephalic pain can fall into any of a wide variety of classes including, for example, vascular headaches (e.g., a migraine headache), tension headaches, headaches associated with the use a substance or its withdrawal, and trigeminal autonomic cephalalgias. The trigeminal autonomic cephalalgias often induce some of the most severe types of cephalic pain of any disorder associated with cephalic pain. Examples of trigeminal autonomic cephalalgias are episodic and chronic cluster headaches, episodic and chronic paroxysmal hemicranias, and short-lasting unilateral neuralgiform headache attacks with conjunctival injection and tearing.

Cluster headaches (also known as migrainous neuralgia, Horton's syndrome, Raeder's syndrome, sphenopalatine neuralgia, and histaminic cephalalgia) are recurrent headaches characterized by sudden onset and intense pain on one side of the face that begins around the eye, temple, or cheek. There are two clinical patterns of cluster headaches: episodic and chronic. About 80-90% of patients with cluster headaches have them in episodic patterns which are characterized by one to three short attacks, e.g., lasting from fifteen minutes to three hours, of pain around the eyes per day which are grouped or "clustered" over a stretch of one to two months and then followed by a pain-free remission period. Typically, the remission period lasts for at least one month and often up to a year. The remaining 10% of patients with cluster headaches have them in chronic patterns which are characterized by daily occurrences of headaches lasting for more than a year with no remission period or with remission periods lasting less than one month. Isselbacher, K. J. et al. (eds). Harrison's Principles of Internal Medicine, Thirteenth Edition (1994, McGraw-Hill, New York, N.Y.), pp. 69-70. A single person may experience alternating episodic and chronic phases of cluster headaches.

While the underlying cause of cluster headaches is unknown, the occurrence of such headaches is correlated with abnormal activation of the posterior hypothalamus. May, A. et al. (1998) *Lancet* 352(9124):275-278. Abnormal hypothalamic activation then does two things. First, it activates the trigeminal nerve, causing pain in the trigeminal distribution. Second, it causes sympathetic dysfunction in the form of drooping eyelid and constricted pupil, and parasympathetic overactivity that is responsible for the runny eye and stuffy nose that accompany most attacks. Sewell, R. A., Halpern, J. H. "Response of Cluster Headache to Psilocybin and LSD." in Winkelman, M. J. et al. eds. Psychedelic Medicine: New Evidence for Hallucinogenic Substances as Treatments (Greenwood Publishing Group, New York, 2007).

Because the pain of a cluster headache comes on suddenly and may subside within a short time, over-the-counter pain relievers such as aspirin or ibuprofen are not effective in treating the pain. The headache is usually gone before these medications can provide pain relief. At present, there are several different approaches for providing acute pain relief for patients suffering from cluster headaches. These approaches include: (1) treatment comprising inhalation of oxygen; (2) treatment with an oral, injectable, or inhalable (e.g., as a nasal spray) form of a triptan; (3) treatment with an intravenous, injectable, or inhalable form of an ergot derivative; (4) treatment with an injectable form of a synthetic somatostatin; and (5) treatment using nasal drops of local anesthetics. All of these acute treatments have disadvantages. For example, while inhalation of 100% oxygen through a mask can provide dramatic relief for most who use it, it can be extremely inconvenient to have to carry around an oxygen cylinder and regulator. In addition, use of triptans is not recommended for people with uncontrolled high blood pressure or ischemic heart disease. While intravenous treatment with ergot derivatives can be fast acting, it must be provided in a doctor's office. Moreover, inhaled versions of ergot derivatives work more slowly and may not provide pain relief in a relevant time frame. Synthetic somatostatins and local anesthetics work for some people but are not reliably effective.

For patients with chronic cluster headaches who do not respond to any of these treatment approaches and, who if left without treatment often kill themselves (hence the informal term of "suicide headache" to characterize a cluster headache), surgery may be indicated. Sewell, R. A., Halpern, J. H. "Response of Cluster Headache to Psilocybin and LSD." in Winkelman, M. J. et al. eds. Psychedelic Medicine: New Evidence for Hallucinogenic Substances as Treatments (Greenwood Publishing Group, New York, 2007). Candidates for surgery must have headaches only on one side of the head because the surgery can be performed only once. Several types of surgery have been used to treat cluster headaches and they typically involve procedures attempting to damage the nerve pathways thought to be the immediate cause of the pain. The most common of these procedures are directed at the trigeminal nerve and include conventional surgery, in which the surgeon cuts part of the trigeminal nerve with a scalpel or uses small burns to destroy part of the nerve, and radiosurgery, in which the surgeon using a focused beam of radiation to destroy part of the trigeminal nerve. Residual muscle weakness in the jaw and sensory loss in certain areas of the face and head often make these procedures options of last resort. Cohen, A. S. et al. (June 2007) *Headache* 969-980; Franzini, A. et al. (May 2003) *Neurosurgery* 52(5):1095-1099.

There are also various options for short-term and long-term prevention of cluster headaches. These treatment options, which also all have disadvantages, include: (1) treatment with corticosteroids (indicated for short term use only as they have serious side effects (e.g., immunosuppression, osteoporosis, cataracts, and psychosis) if used long-term; (2) treatment with ergot derivatives, provided sublingually or rectally (indicated for short term use of two to three weeks only); (3) treatment with injectable nerve blockers (indicated for short-term use and must be administered in a doctor's office); (4) treatment with anticonvulsants (indicated for both short and long term use); (5) treatment with methysergide (indicated for short term use only as prolonged treatment has been associated with rare fibrotic conditions); (6) treatment with calcium channel blockers (indicated for both short and long term use but has many side effects including dizziness, nausea, fatigue, swelling of the ankles and low blood pressure); (7) treatment with serotonin agonists (insurance generally covers only a handful of injections per month, not the required several a day, and the too frequent use of such compounds can have cardiac implications); (8) treatment with lithium (indicated for long term use but has many side effects such as tremor, increased thirst, diarrhea and drowsiness and can cause kidney and thyroid damage). Cohen, A. S. et al. (June 2007) *Headache* 969-980; Sewell, R. A., Halpern, J. H. "Response of Cluster Headache to Psilocybin and LSD." in Winkelman, M. J. et al. eds. Psychedelic Medicine: New Evidence for Hallucinogenic Substances as Treatments (Greenwood Publishing Group, New York, 2007); http://www.mayoclinic.com/health/cluster-headache/DS00487. Thus, there exists a need for new medications and methods of treatment and/or prevention using medications which avoid some of the disadvantages experienced by patients using these traditional treatment methods.

SUMMARY OF THE INVENTION

The present invention is directed to various compositions and methods for preventing and treating disorders associated with cephalic pain. Compositions of the invention include ergoline derivatives, e.g., substantially pure forms of ergoline derivatives, e.g., substantially pure forms of lysergic acid amide (LSA, also known as ergine) and 2-bromo-LSD. Exemplary ergoline derivatives include those described herein, for example, compounds of formulas (I) and (Ia). In some embodiments, the ergoline derivative is LSA, ergonovine, methergine, methysergide, or lysergic acid diethylamide (LSD), e.g., 2-bromo-LSD. In some embodiments, the ergoline derivative is not methergine. In some embodiments, the ergoline derivative is not methysergide. In some embodiments, the ergoline derivative is neither methergine nor methysergide. In some embodiments, the ergoline derivative is a peptide alkaloid, such as ergotamine, dihydroergotamine ergocristine, ergocornine, ergocryptine, bromocriptine, or ergovaline. In some embodiments the peptide alkaloid is not dihydroergotamine. In some embodiment, the peptide alkaloid is not ergotamine. In some embodiments, the peptide alkaloid is neither dihydroergotamine nor ergotamine. In some embodiments, when the method of the invention for preventing or treating disorders associated with cephalic pain are those in which the ergoline derivative, e.g., LSA, 2-bromo-LSD, is used in combination with another therapeutic agent described herein, the ergoline derivative, e.g., LSA, 2-bromo-LSD, is not in substantially pure form. In other embodiments, when the method of the invention for preventing or treating disorders associated with cephalic pain are those in which the ergoline derivative, e.g., LSA, 2-bromo-LSD, is used in combination with another therapeutic agent described herein, the ergoline derivative, e.g., LSA, 2-bromo-LSD, is in substantially pure form.

The ergoline derivatives are provided in amounts effective, e.g., in an amount between about 50 µg and about 5000 µg, e.g., in an amount between 100 µg and about 4000 µg, e.g., in an amount between about 100 µg and about 3000 µg, e.g., in an amount between about 100 µg and about 2000 µg, to prevent or treat disorders associated with cephalic pain. These compositions can further include pharmaceutically acceptable carriers. In certain aspects of the invention, the compositions and pharmaceutical compositions are formulated such that they are suitable for various routes of administration. In one embodiment, the compositions are produced in a form suitable for parenteral administration, e.g., subcutaneous administration, intravenous administration, intramuscular administration, and transmucosal administration such as sublingual administration, rectal administration, or vaginal administration. In another embodiment, the compositions are produced in a form suitable for enteral administration, e.g., oral administration.

The compositions of the invention can be provided in therapeutic packages for dispensing to, or for use in dispensing to, a subject, e.g., a human, with a disorder associated with cephalic pain. The therapeutic packages typically contain a substantially pure form of an ergoline derivative, e.g., LSA, 2-bromo-LSD, of the invention, in one or more unit dosage forms or in a multiple dosage form, suitable for parenteral or enteral administration as well as a container containing the ergoline derivative in one or more unit dosage forms or in multiple dosage form. In certain embodiments, the therapeutic packages also include a package insert or other United States Food and Drug Administration (FDA) approved label or document which indicates to physicians and/or purchasers that the ergoline derivative enclosed therein, when administered as instructed on the package insert or FDA approved label or document, is effective in preventing or treating a disorder, e.g., cluster headache, associated with cephalic pain.

Another aspect of the invention is a method for treating a disorder associated with cephalic pain which comprises administering, e.g, enterally, e.g., orally, or parenterally, e.g., subcutaneously, intravenously, transmucosally (e.g., sublingually, buccally, rectally or vaginally) to a subject in need of such treatment a therapeutically effective amount of an ergoline derivative, e.g., LSA, e.g., a substantially pure form of LSA, 2-bromo-LSD, e.g., a substantially pure form of 2-bromo-LSD, of the invention. In one embodiment, the subject in need of such treatment is a human who suffers from, is suffering from, or is susceptible to a disorder associated with cephalic pain. One class of disorders associated with cephalic pain includes the disorders which have been characterized as the trigeminal autonomic cephalalgias. Examples of trigeminal autonomic cephalalgias that can be treated according to the present invention are episodic and chronic cluster headache (CH), episodic and chronic paroxysmal hemicrania (PH), and short-lasting unilateral neuralgiform headache attacks with conjunctival injection and tearing (SUNCT). In another embodiment, the disorder associated with cephalic pain is vascular headache (e.g., a migraine headache), a tension headache, or a headache associated with the use of a substance (e.g., triptans such as sumatriptan, benzodiazepines such as alprazolam, analgesics such as ibuprofen, ergots such as ergotamine, opioids such as morphine, recreational drugs such as caffeine, nicotine, alcohol, and hormone replacement therapy containing, for example, estrogen) or its withdrawal. The ergoline derivatives are provided in therapeutically effective amounts (i.e., amounts effective to treat a disorder associated with cephalic pain, e.g., in an amount between about 100 µg and about 5.0 mg, e.g., in an amount between 200 µg and about 2.0 mg, e.g., in an amount between about 200 µg about 1.0 mg), to treat disorders associated with cephalic pain.

The methods of the invention can further include administering to the subject a second compound which acutely relieves at least one symptom of a disorder associated with cephalic pain, e.g., administering a compound described herein in combination with a second compound. Examples of second compounds which acutely relieve at least one symptom of a disorder associated with cephalic pain include oxygen, serotonin receptor agonists (e.g., triptans such as sumatriptan, eletriptan, rizatriptan, frovatriptan, almotriptan, zolmitriptan, and naratriptan), ergot derivatives (e.g., dihydroergotamine, and ergotamine tartrate), hormones (e.g., corticosteroids (e.g., prednisone, cortisol), testosterone, growth hormone, luteinizing hormone, somatostatin, and prolactin), and local anesthetics (e.g., amino ester local anesthetics (e.g., benzocaine, chloroprocaine, cocaine, procaine, and tetracaine/amethocaine), amino amide local anesthetics (e.g., bupivacaine levobupiva, lidocaine/lignocaine, mepivacaine, prilocalne, ropivacaine, articaine, trimecaine, and combinations thereof (e.g., lidocaine and prilocalne, in the case of local anesthetics). Alternatively, or in addition to administering such shorter acting second compounds, other compounds, e.g., longer acting compounds, for use in treating a disorder associated with cephalic pain can be administered with the ergoline derivatives of the invention. In this embodiment, such compounds include lithium, melatonin, calcium channel blockers (e.g., verapamil, diltiazem, nifedipine, nimodipine), hormones (see examples described herein), anticonvulsant agents (e.g., topiramate, valproic acid, gabapentin), opioid receptor antagonists (e.g., naltrexone hydrochloride, naloxone, buprenorphine, nalmefene, nalorphone) and sedatives (e.g., benzodiazepines, barbiturates, meclobamate, chloral hydrate, sodium oxybate).

In the methods of the present invention, the ergoline derivatives, e.g., LSA, e.g., substantially pure forms of LSA, 2-bromo-LSD, e.g., substantially pure forms of 2-bromo-LSD, and/or the other compounds, e.g., longer acting compounds or the shorter acting compounds, described herein can be administered at least once a day, at least once every other day, at least once every two days, at least once every three days, at least once every four days, or at least once every five days or more. In one embodiment, the ergoline derivative and/or the additional or other compound are/is administered on one of these schedules and at least three times or for at least three days. In certain embodiments, the subject, e.g., a human, has not received a headache medication (e.g., the subject has undergone a "washout" period in which he or she has been weaned from any headache medication) for at least one day, two days, three days, four days, or five days prior to administration of the ergoline derivative and/or the additional or other compound.

Other aspects of the invention include methods for treating a disorder associated with cephalic pain which comprise administering to a subject, e.g., a human, e.g., a human who has not received a headache medication for at least five days, in need of such treatment a therapeutically effective amount of an ergoline derivative, e.g., LSA, e.g., a substantially pure form of LSA, 2-bromo-LSD, e.g., a substantially pure form of 2-bromo-LSD, and a therapeutically effective amount of an opioid receptor antagonist. The ergoline derivative and the opioid receptor antagonist can be administered concurrently or sequentially (e.g., either the ergoline derivative is administered prior to the opioid receptor antagonist or the opioid receptor antagonist is administered prior to the ergoline derivative). The ergoline derivative and the opioid receptor antagonist can be administered by any of the routes (and by the same or different routes) described herein at least once a day for at least three days. In addition, any of the short acting compounds described herein can also be administered with the ergoline derivative and the opioid receptor antagonist. In one embodiment, such short acting compound administered with the ergoline derivative and the opioid receptor antagonist is oxygen.

Yet other aspects of the invention include methods for preventing, e.g., extending remission periods of, a disorder associated with cephalic pain in a subject in need thereof, which comprise administering to the subject a therapeutically effective amount of an ergoline derivative, e.g., LSA, e.g., a substantially pure form of LSA, 2-bromo-LSD, e.g, a substantially pure form of 2-bromo-LSD, during a period in which the subject is not suffering from cephalic pain. Examples of disorders associated with cephalic pain which can be prevented according to the method of the present invention include trigeminal autonomic cephalalgias such as episodic and chronic (CH), episodic and chronic (PH), and SUNCT. In one embodiment, the ergoline derivative is administered to a subject who suffers from a trigeminal autonomic cephalalagia, e.g., CH, and is in a remission period. Other examples of disorders associated with cephalic pain which can be prevented according to the method of the present invention include vascular headache (e.g., a migraine headache), a tension headache, and a headache associated with the use of a substance or its withdrawal. To prevent a disorder associated with cephalic pain, a subject can be administered a therapeutically effective amount, as described herein, of an ergoline derivative, as described herein, at least once a week, at least once every two weeks, at least once every three weeks, at least once every four weeks, at least once every two months, or at least once every three months or more. Other compounds which are used to treat disorders associated with cephalic pain, including, for example, lithium, melatonin, calcium channel blockers, hormones, anticonvulsant agents, opioid receptor antagonists, and sedatives, as described herein, can be administered with the ergoline derivative to prevent such disorders (e.g., to extend remission periods).

DETAILED DESCRIPTION OF THE PREFERRED EMBODIMENTS

The present invention is directed to compositions and methods for use in the prevention and/or treatment of disorders associated with cephalic pain. Typically, the compositions include at least one ergoline derivative, e.g., an ergoline derivative in substantially pure form. As used herein, the term "ergoline derivative" refers to a compound of formula (I) or formula (Ia), and pharmaceutically acceptable salts thereof.

In some embodiments, the ergoline derivative is a compound of formula (I),

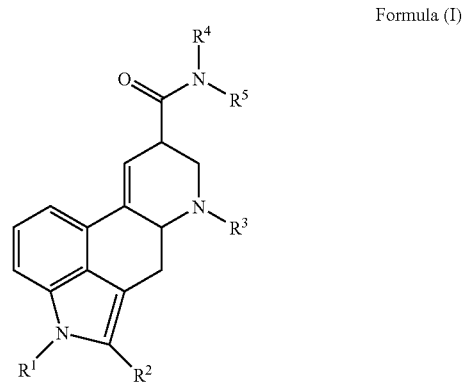

Formula (I)

wherein
$R^1$ is H, $C_1$-$C_6$ alkyl, or a nitrogen protecting group;
$R^2$ is H or halo;
$R^3$ is H, $C_1$-$C_6$ alkyl, or a nitrogen protecting group; (in some preferred embodiments, $R^2$ is methyl)
each $R^4$ and $R^5$ are independently H, $C_1$-$C_6$ alkyl, optionally substituted with $R^6$; or and wherein $R^6$ is —OH, or one of $R^4$ or $R^5$ is

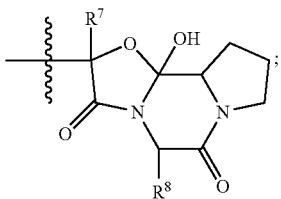

$R^7$ is $C_1$-$C_6$ alkyl;
$R^8$ is $C_1$-$C_6$ alkyl or arylalkyl.

In some embodiments, $R^1$ is H or $C_1$-$C_6$ alkyl; $R^2$ is H; $R^3$ is H or $C_1$-$C_6$ alkyl; (in some highly preferred embodiments, $R^3$ is methyl); each $R^3$ and $R^4$ are independently H, $C_1$-$C_6$ alkyl, optionally substituted with $R^6$; and $R^6$ is —OH.

In some embodiments, $R^1$ is H or $C_1$-$C_6$ alkyl; $R^2$ is methyl; each $R^4$ and $R^5$ are independently H, $C_1$-$C_6$ alkyl, optionally substituted with $R^5$; and $R^5$ is —OH.

In some embodiments, $R^1$ is H or methyl.

In some embodiments, $R^2$ is H. In some embodiments, $R^2$ is halo, for example, bromo.

In some embodiments $R^3$ is methyl.

In some embodiments, $R^4$ is H. In some embodiments $R^4$ is alkyl, for example, a branched alkyl. In some embodiments, $R^4$ is alkyl substituted with OH. In some embodiments, $R^4$ is a branched alkyl substituted with OH. In some embodiments, $R^4$ is

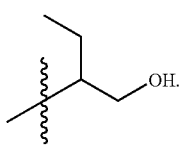 [SMILES: *C(CC)CO]

In some embodiments, $R^4$ is

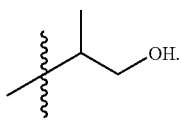

In some embodiments, $R^4$ is ethyl.

In some embodiments, $R^5$ is H. In some embodiments, $R^5$ is ethyl. In some embodiments, both $R^4$ and $R^5$ are H. In some embodiments, both $R^4$ and $R^5$ are ethyl. In some embodiments, $R^4$ alkyl substituted with OH and $R^5$ is H.

In some embodiments, $R^4$ is

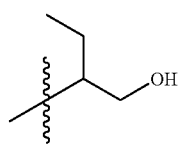 [SMILES: *C(CC)CO]

and $R^5$ is H. In some embodiments, $R^4$ is

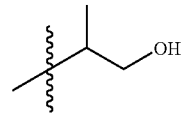 [SMILES: *C(C)CO]

and $R^5$ is H. In some embodiments, $R^4$ is H; and $R^5$ is

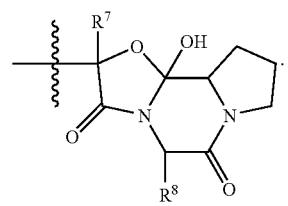

In some preferred embodiments, $R^1$, $R^2$, $R^4$ and $R^5$ are each H, and $R^5$ is methyl (i.e., LSA, ergine).

In some preferred embodiments, $R^1$, $R^2$, and $R^5$ are each H, $R^4$ is

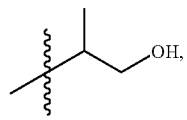

and $R^3$ is methyl (i.e., ergonovine).

In some preferred embodiments, $R^1$, $R^2$, and $R^5$ are each H, $R^4$ is

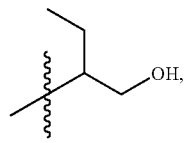

and $R^3$ is methyl (i.e., methergine).

In some preferred embodiments, $R^1$ and $R^3$ are each methyl, $R^4$ is

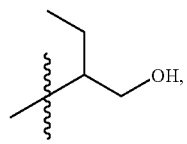

and $R^5$ and $R^2$ are each H (i.e., methylsergide).

In some preferred embodiments, $R^1$ and $R^2$ are each H, $R^3$ is methyl, and each of $R^4$ and $R^5$ are ethyl (i.e., LSD).

In some embodiments, $R^1$ is H, or $C_1$-$C_6$ alkyl, or a nitrogen protecting group; $R^2$ is H or halo; $R^3$ is H, or $C_1$-$C_6$ alkyl, or a nitrogen protecting group; $R^4$ is H;

$R^5$ is

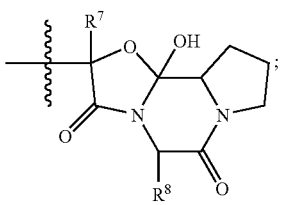

$R^7$ is $C_1$-$C_6$ alkyl; and $R^8$ is $C_1$-$C_6$ alkyl or arylalkyl.

In some embodiments, $R^1$ is H; $R^2$ is H or halo; $R^3$ is H, or $C_1$-$C_6$ alkyl, or a nitrogen protecting group; $R^4$ is H; $R^5$ is

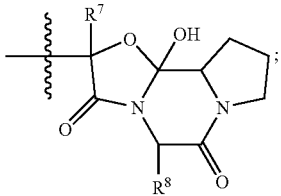

$R^7$ is $C_1$-$C_6$ alkyl; and $R^8$ is $C_1$-$C_6$ alkyl or arylalkyl.

In some embodiments, $R^1$ is H, or $C_1$-$C_6$ alkyl, or a nitrogen protecting group; $R^2$ is H or halo; $R^3$ is $C_1$-$C_6$ alkyl; $R^4$ is H; $R^5$ is

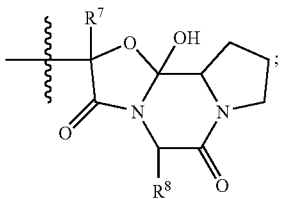

$R^7$ is $C_1$-$C_6$ alkyl; and $R^8$ is $C_1$-$C_6$ alkyl or arylalkyl.

In some embodiments, $R^7$ is a branched $C_1$-$C_6$ alkyl. In some embodiments, $R^7$ is

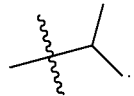

In some embodiments, $R^7$ is methyl.

In some embodiments, $R^8$ is $C_1$-$C_6$ alkyl. In some embodiments, $R^8$ is a branched $C_1$-$C_6$ alkyl. In some embodiments, $R^8$ is

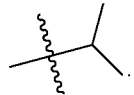

In some embodiments, $R^8$ is

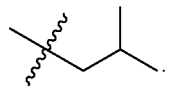

In some embodiments, $R^8$ is arylalkyl. In some embodiments, $R^8$ is benzyl.

In some preferred embodiments, $R^1$ is H; $R^2$ is H or halo; $R^3$ is methyl; $R^4$ is H; $R^5$ is

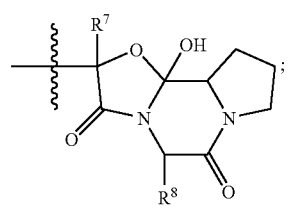

$R^7$ is $C_1$-$C_6$ alkyl; and $R^8$ is $C_1$-$C_6$ alkyl or arylalkyl. In some embodiments, $R^2$ is H. In some embodiments, $R^2$ is bromo. In some embodiments, $R^7$ is methyl. In some embodiments, $R^7$ is

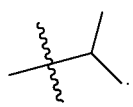 [SMILES: *C(C)C]

In some embodiments, $R^8$ is

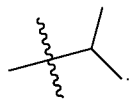

In some embodiments, $R^8$ is

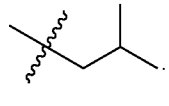

In some embodiments, $R^8$ is benzyl.

In some embodiments, $R^1$, $R^2$, and $R^4$ are each H; $R^5$ is

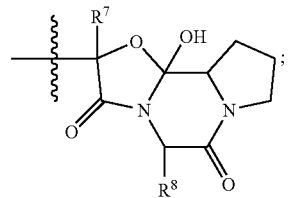

$R^3$ and $R^7$ are each methyl; and $R^8$ is benzyl (i.e., ergotamine).

In some embodiments, $R^1$, $R^2$, and $R^4$ are each H; $R^3$ is methyl; $R^5$ is

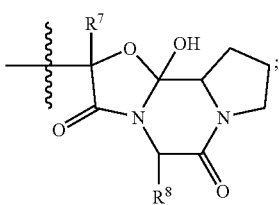

R⁷ is

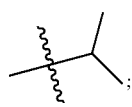 [SMILES: *C(C)C]

and R⁸ is benzyl (i.e., ergocristine).

In some embodiments, R¹, R², and R⁴ are each H; R³ is methyl; R⁵ is

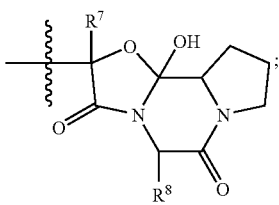

and R⁷ and R⁸ are each

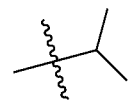 [SMILES: *C(C)C]

(i.e., ergocornine).

In some embodiments, R¹, R², and R⁴ are each H; R³ is methyl; R⁵ is

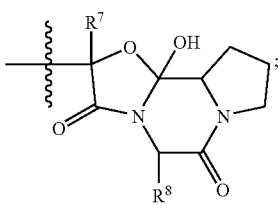

R⁷ is

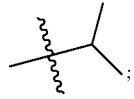 [SMILES: *C(C)C]

and R⁸ is

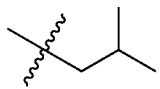 [SMILES: *CC(C)C]

(i.e., ergocryptine).

In some embodiments, R¹ and R⁴ are each H; R² is bromo; R³ is methyl; R⁵ is

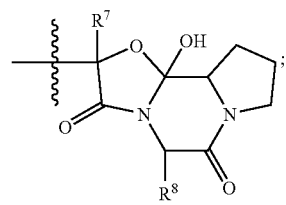

R⁷ is

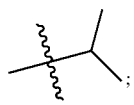

and R⁸ is

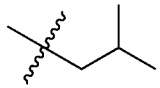 [SMILES: *CC(C)C]

(i.e., bromocriptine).

In some embodiments, R¹, R², and R⁴ are each H; R⁵ is

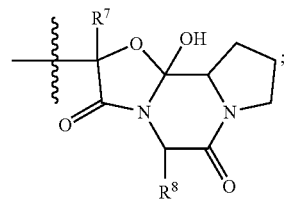

R³ and R⁷ are each methyl; and R⁸ is

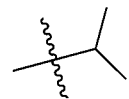

(i.e. ergovaline).

In some embodiments, the invention features a composition comprising a compound of formula (Ia), wherein the compound has an enantiomeric excess of at least about 60% of the compound of formula (Ia)

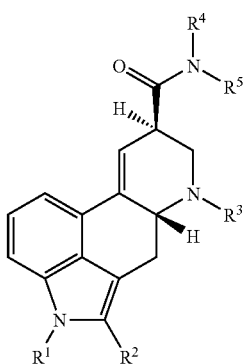

Formula (Ia)

wherein
$R^1$ is H, $C_1$-$C_6$ alkyl, or a nitrogen protecting group;
$R^2$ is H or halo;
$R^3$ is H, $C_1$-$C_6$ alkyl, or a nitrogen protecting group; (in some preferred embodiments, $R^2$ is methyl)
each $R^4$ and $R^5$ are independently H, $C_1$-$C_6$ alkyl, optionally substituted with $R^6$; or and
wherein $R^6$ is —OH, or one of $R^4$ or $R^5$ is

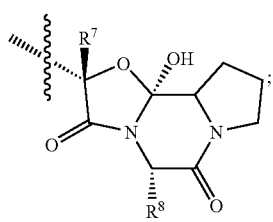

$R^7$ is $C_1$-$C_6$ alkyl;
$R^8$ is $C_1$-$C_6$ alkyl or arylalkyl.
In some embodiments, $R^1$ is H or $C_1$-$C_6$ alkyl; $R^2$ is H; $R^3$ is H or $C_1$-$C_6$ alkyl; (in some highly preferred embodiments, $R^3$ is methyl); each $R^3$ and $R^4$ are independently H, $C_1$-$C_6$ alkyl, optionally substituted with $R^6$; and $R^6$ is —OH.
In some embodiments, $R^1$ is H or $C_1$-$C_6$ alkyl; $R^2$ is methyl; each $R^4$ and $R^5$ are independently H, $C_1$-$C_6$ alkyl, optionally substituted with $R^5$; and $R^5$ is —OH.
In some embodiments, $R^1$ is H or methyl.
In some embodiments, $R^2$ is H. In some embodiments, $R^2$ is halo, for example, bromo.
In some embodiments $R^3$ is methyl.
In some embodiments, $R^4$ is H. In some embodiments $R^4$ is alkyl, for example, a branched alkyl. In some embodiments, $R^4$ is alkyl substituted with OH. In some embodiments, $R^4$ is a branched alkyl substituted with OH. In some embodiments, $R^4$ is

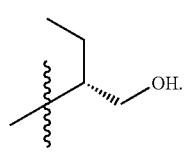

In some embodiments, $R^4$ is

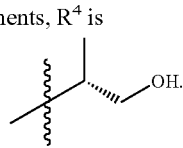

In some embodiments, $R^4$ is ethyl.
In some embodiments, $R^5$ is H. In some embodiments, $R^5$ is ethyl. In some embodiments, both $R^4$ and $R^5$ are H. In some embodiments, both $R^4$ and $R^5$ are ethyl. In some embodiments, $R^4$ alkyl substituted with OH and $R^5$ is H.
In some embodiments, $R^4$ is

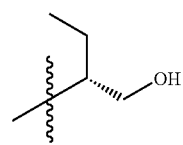 [SMILES: *[C@H](CC)CO]

and $R^5$ is H. In some embodiments, $R^4$ is

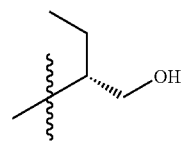 [SMILES: *[C@H](CC)CO]

and $R^5$ is H. In some embodiments, $R^4$ is H; and $R^5$ is

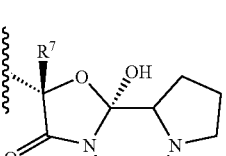

In some preferred embodiments, $R^1$, $R^2$, $R^4$ and $R^5$ are each H, and $R^3$ is methyl (i.e., LSA, ergine).
In some preferred embodiments, $R^1$, $R^2$, and $R^5$ are each H, $R^4$ is

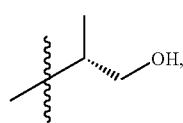

and $R^3$ is methyl (i.e., ergonovine).
In some preferred embodiments, $R^1$, $R^2$, and $R^5$ are each H, $R^4$ is

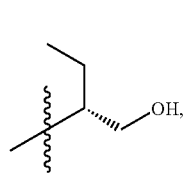

and $R^3$ is methyl (i.e., methergine).

In some preferred embodiments, $R^1$ and $R^3$ are each methyl, $R^4$ is

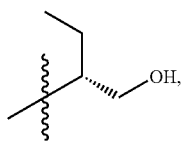

and $R^5$ and $R^2$ are each H (i.e., methysergide).

In some preferred embodiments, $R^1$ and $R^2$ are each H, $R^3$ is methyl, and each of $R^4$ and $R^5$ are ethyl (i.e., LSD).

In some embodiments, $R^1$ is H, or $C_1$-$C_6$ alkyl, or a nitrogen protecting group; $R^2$ is H or halo; $R^3$ is H, or $C_1$-$C_6$ alkyl, or a nitrogen protecting group; $R^4$ is H; $R^5$ is

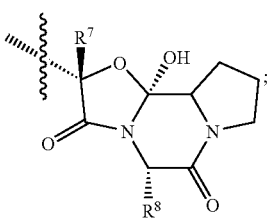

$R^7$ is $C_1$-$C_6$ alkyl; and $R^8$ is $C_1$-$C_6$ alkyl or arylalkyl.

In some embodiments, $R^1$ is H; $R^2$ is H or halo; $R^3$ is H, or $C_1$-$C_6$ alkyl, or a nitrogen protecting group; $R^4$ is H; $R^5$ is

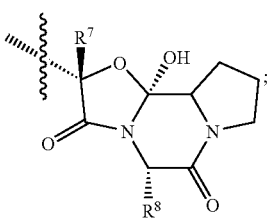

$R^7$ is $C_1$-$C_6$ alkyl; and $R^8$ is $C_1$-$C_6$ alkyl or arylalkyl.

In some embodiments, $R^1$ is H, or $C_1$-$C_6$ alkyl, or a nitrogen protecting group; $R^2$ is H or halo; $R^3$ is $C_1$-$C_6$ alkyl; $R^4$ is H; $R^5$ is

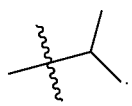

$R^7$ is $C_1$-$C_6$ alkyl; and $R^8$ is $C_1$-$C_6$ alkyl or arylalkyl.

In some embodiments, $R^7$ is a branched $C_1$-$C_6$ alkyl. In some embodiments, $R^7$ is

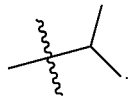

In some embodiments, $R^7$ is methyl.

In some embodiments, $R^8$ is $C_1$-$C_6$ alkyl. In some embodiments, $R^8$ is a branched $C_1$-$C_6$ alkyl. In some embodiments, $R^8$ is

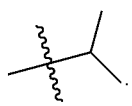

In some embodiments, $R^8$ is

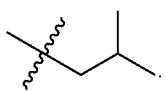

In some embodiments, $R^8$ is arylalkyl. In some embodiments, $R^8$ is benzyl.

In some preferred embodiments, $R^1$ is H; $R^2$ is H or halo; $R^3$ is methyl; $R^4$ is H; $R^5$ is

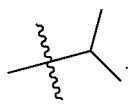 [SMILES: *C(C)C ; "."]

$R^7$ is $C_1$-$C_6$ alkyl; and $R^8$ is $C_1$-$C_6$ alkyl or arylalkyl. In some embodiments, $R^2$ is H. In some embodiments, $R^2$ is bromo. In some embodiments, $R^7$ is methyl. In some embodiments, $R^7$ is

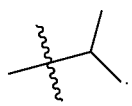

In some embodiments, $R^8$ is

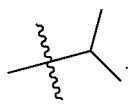 [SMILES: *C(C)C ; "."]

In some embodiments, $R^8$ is

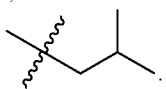

In some embodiments, $R^8$ is benzyl.

In some embodiments, $R^1$, $R^2$, and $R^4$ are each H; $R^5$ is

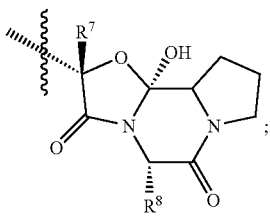

$R^3$ and $R^7$ are each methyl; and $R^8$ is benzyl (i.e., ergotamine).

In some embodiments, $R^1$, $R^2$, and $R^4$ are each H; $R^3$ is methyl; $R^5$ is

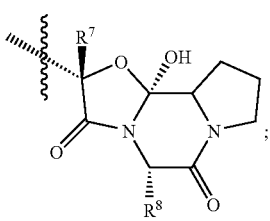

$R^7$ is

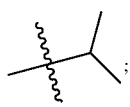

and $R^8$ is benzyl (i.e., ergocristine).

In some embodiments, $R^1$, $R^2$, and $R^4$ are each H; $R^3$ is methyl; $R^5$ is

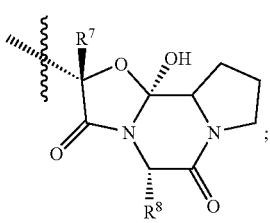

and $R^7$ and $R^8$ are each

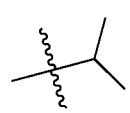 [SMILES: *C(C)C]

(i.e., ergocornine).

In some embodiments, $R^1$, $R^2$, and $R^4$ are each H; $R^3$ is methyl; $R^5$ is

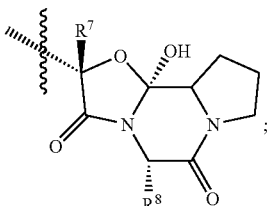

$R^7$ is

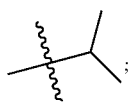 [SMILES: *C(C)C ; ";"]

and $R^8$ is

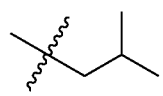 [SMILES: *CC(C)C]

(i.e., ergocryptine).

In some embodiments, $R^1$ and $R^4$ are each H; $R^2$ is bromo; $R^3$ is methyl; $R^5$ is

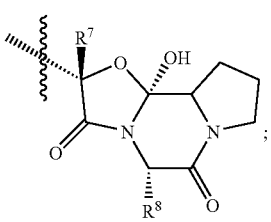

$R^7$ is

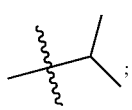

and $R^8$ is

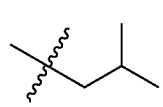 [SMILES: *CC(C)C]

(i.e., bromocriptine).

In some embodiments, $R^1$, $R^2$, and $R^4$ are each H; $R^5$ is

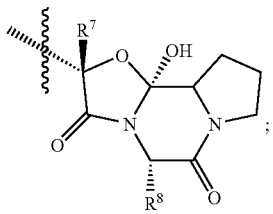

$R^3$ and $R^7$ are each methyl; and $R^8$ is

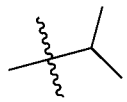 [SMILES: *C(C)C]

(i.e., ergovaline).

In some embodiments, the invention features a composition comprising a compound of formula (Ia), wherein the compound has an enantiomeric excess of at least about 65% of the compound of formula (Ia), e.g., at least about 70%, at least about 75%, at least about 80%, at least about 85%, at least about 90%, at least about 95%, at least about 98%, at least about 99%.

Preferred ergoline derivatives are LSA, ergonovine, methergine, methysergide, LSD, and 2-bromo-LSD. Preferred ergoline derivatives also include peptide alkaloids, such as ergotamine, ergocristine, ergocomine, ergocryptine, bromocriptine, or ergovaline.

The compounds of this invention can contain one or more asymmetric centers and thus occur as racemates and racemic mixtures, single enantiomers, individual diastereomers and diastereomeric mixtures. All such isomeric forms of these compounds are expressly included in the present invention. The compounds of this invention can also contain linkages (e.g., carbon-carbon bonds) or substituents that can restrict bond rotation, e.g., restriction resulting from the presence of a ring or double bond. Techniques useful for the separation of isomers, e.g., stereoisomers are within skill of the art and are described in Eliel, E. L.; Wilen, S. H.; Mander, L. N. Stereochemistry of Organic Compounds, Wiley Interscience, NY, 1994. For example a stereoisomer of a compound described herein can be resolved to a high enantiomeric excess (e.g., 60%, 70%, 80%, 85%, 90%, 95%, 99% or greater) via formation of diasteromeric salts, e.g., with a chiral base, e.g., (+) or (−) a-methylbenzylamine, or via high performance liquid chromatography using a chiral column.

In some instances, a compound disclosed herein is administered (for example, in a composition) where one isomer (e.g., the R isomer or S isomer) is present in high enantiomeric excess.

The compounds described herein include the compounds themselves, as well as their salts. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Pharmaceutically acceptable salts of the compounds described herein include those derived from pharmaceutically acceptable inorganic and organic acids and bases.

Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds described herein and their pharmaceutically acceptable acid addition salts.

Salts derived from appropriate bases include alkali metal (e.g., sodium), alkaline earth metal (e.g., magnesium), ammonium and N-(alkyl)4 salts. The compounds described herein also include the quaternization of any basic nitrogen-containing groups of the compounds disclosed herein. Water or oil-soluble or dispersible products can be obtained by such quaternization. Salt forms of the compounds of any of the compounds described herein can be amino acid salts of carboxy groups (e.g. L-arginine, -lysine, -histidine salts).

In some embodiments, a compound described herein includes a prodrug of that compound. Examples of prodrugs include esters and other pharmaceutically acceptable derivatives, which, upon administration to a subject, are capable of providing active compounds. The compounds described herein can be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, C1-C12 alkyl indicates that the group may have from 1 to 12 (inclusive) carbon atoms in it.

The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "nitrogen protecting group" refers to a moiety that is positioned on a nitrogen atom of a compound described herein. The compound protects the nitrogen from participating in a chemical reaction under certain conditions and can be readily removed, thus providing the unprotected, free nitrogen atom. An example of a nitrogen protecting group includes, but is not limited to, tert-butoxycarbonyl.

As used herein, a "substantially pure form of" a compound described herein, e.g., an ergoline derivative, e.g., LSA, 2-bromo-LSD, refers to a composition, in liquid or solid form, containing at least about 50 weight percent, more preferably at least about 60 weight percent, yet more preferably at least about 70 weight percent, even more preferably at least about 80, 81, 82, 83, 84, 85, 86, 87, 88, or 89 weight percent, and most preferably at least about 90, 91, 92, 93, 94, 95, 96, 97, 98, 99, or 100 weight percent of the compound, e.g., the ergoline derivative, e.g., LSA, 2-bromo-LSD, based on the total weight of the composition.

In some embodiments, an ergoline derivative, such as a compound described herein, is found in nature, as a component of a natural product and in the presence of other alkaloids. In some embodiments, an ergoline derivative described herein is a component of a mixture that includes one or more other components, for example a non-ergoline derivative alkaloid.

In some embodiments, a composition comprising an ergoline derivative described herein is substantially free of non-ergoline derivative alkaloids. As used herein, "substantially free" when referring to a composition, liquid or solid, of an ergoline derivative as described herein, means the composition, liquid or solid contains less than about 50 weight percent of another component such as a non-ergoline derivative alkaloid, more preferably less than about 40, weight percent, yet more preferably less than about 30 weight percent, even more preferably less than about 20, 19, 18, 17, 16, 15, 14, 13, 12, or 11 weight percent, and most preferably less than about 10, 9, 8, 7, 6, 5, 4, 3, 2, or 1 weight percent of another component such as a non-ergoline derivative alkaloid.

The ergoline derivatives and pharmaceutically acceptable salts thereof of the invention can be admixed or combined with a pharmaceutically acceptable carrier to produce pharmaceutical compositions. As used herein, a "pharmaceutically acceptable carrier" refers to a pharmaceutically acceptable material, composition or vehicle, suitable for administration to mammals, e.g., humans. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the subject.

Forms suitable for parenteral administration include subcutaneous, intracutaneous, intravenous, intramuscular, intraarticular, intraarterial, intrasynovial, intrasternal, intrathecal, intralesional and intracranial injection or infusion techniques.

Forms suitable for enteral administration include any form of administration suitable for delivery to any part of the gastrointestinal tract, including small and large intestines (i.e., the gastrointestinal tract). Methods of enteral administration include oral, sublingual (dissolving the drug under the tongue), and rectal. Exemplary administration forms include tablets, capsules, drops, gastric feeding tube, duodenal feeding tube, gastrostomy, suppository and enema.

As used herein, "administered in combination" or a combined administration of two compounds or agents means that two or more compounds or agents are administered to a subject at the same time or within an interval such that there is overlap of an effect of each agent on the patient. Preferably they are administered within 15, 10, 5, or 1 minute of one another. Preferably the administrations of the compounds or agents are spaced sufficiently close together such that a combinatorial effect is achieved. The compounds or agents can be administered simultaneously, for example in a combined unit dose (providing simultaneous delivery of both agents). Alternatively, the compounds or agents can be administered at a specified time interval, for example, an interval of minutes, hours, days or weeks. Generally, the compounds or agents are concurrently bioavailable, e.g., detectable, in the subject.

In a preferred embodiment, the compounds or agents are administered essentially simultaneously, for example two unit dosages administered at the same time, or a combined unit dosage of the two agents. In another preferred embodiment, the compounds or agents are delivered in separate unit dosages. The compounds or agents can be administered in any order, or as one or more preparations that includes two or more agents. In a preferred embodiment, at least one administration of one of the compounds or agents, e.g., the first compound or agent, is made within minutes, one, two, three, or four hours, or even within one or two days of the other compound or agent, e.g., the second compound or agent. In some cases, combinations can achieve synergistic results, e.g., greater than additive results, e.g., at least 20, 50, 70, or 100% greater than additive.

The invention is also directed to therapeutic packages for dispensing, or for use in dispensing, ergoline derivatives of the invention to a subject with a disorder associated with cephalic pain. Such therapeutic packages are combinations of two or more components which are packed for sale, storage, or transportation at least one component of which is intended for therapeutic use, e.g., intended for therapeutic use in a subject, e.g., a human. Such therapeutic packages can be used to dispense a compound or agent of the invention to a subject to treat or prevent a disorder described herein (e.g., supply to a subject, e.g., supply a compound to a subject, e.g., a human), according to a prescription or other written order issued by a physician or other qualified practitioner that authorizes a pharmacy to supply a specific medication to a subject). In one embodiment of the invention, the therapeutic package comprises (a) an ergoline derivative, e.g., a substantially pure form of an ergoline derivative, e.g., LSA, e.g., LSA in substantially pure form, e.g., 2-bromo-LSD, e.g., a substantially pure form of 2-bromo-LSD, which is in a form suitable for parenteral administration or which is in a form suitable for enteral administration and which is in one or more unit dosage forms or multiple dosage form; and (b) a container containing the ergoline derivative in one or more unit dosage forms or multiple dosage form. In another embodiment, the therapeutic packages can further include a package insert which indicates to physicians and purchasers that the ergoline derivative, e.g., LSA, 2-bromo-LSD, enclosed therein, when administered as instructed on the package insert, is effective in treating or preventing a disorder associated with cephalic pain, e.g., cluster headache.

A unit dosage form of an ergoline derivative or other compound described herein refers to a preparation of such ergoline derivative or other compound in a form specifically for use as a single administration or a single dose. In one embodiment, a unit dosage form of an ergoline derivative of the invention includes from about 25 µg to about 5000 µg. A multiple dosage form of an ergoline derivative or other compound described herein refers to a preparation or preparations of such ergoline derivative or other compounds in a form or forms specifically for use as multiple administrations or multiple doses.

Containers which can be used in the therapeutic packages of the invention are objects which can be used to hold the ergoline derivatives. Such objects include vials, bottles, tubes, syringes (e.g., pre-filled syringes containing one or more doses) or other containers for single or multiple administrations. Such containers can be made of glass or a polymer material such as polypropylene, polyolefin, polyethylene, or polyvinylchloride, for example. Preferred containers can include a seal, or other closure system, such as a rubber stopper that can be penetrated by a needle in order to withdraw a single dose and then re-seal upon removal of the needle. All such containers for injectable liquids, lyophilized formulations, reconstituted lyophilized formulations or reconstitutable powders for injection known in the art are contemplated for use in the present disclosed compositions and methods. The formulations provided herein can be formulated in a variety of concentrations in various vial sizes for various administration dosages. For example, the dosages can be formulated in a ¼, ½, 1 or 2 ml vial, or any other size vial or other container known by one of skill in the art.

Package inserts which can be included in the therapeutic packages of the invention are printed materials or printed documents which include the pharmacologic description of a drug (in this case, the ergoline derivative or other compound described herein) including approved chemical and proprietary names, regulatory authority, e.g., U.S. Food & Drug Administration (FDA), approved indications and usage, contraindications, warnings, precautions, adverse reactions, drug abuse and dependence information, overdosage discussion, dosage and administration, formulations, and appropriate references, all as set forth as required by detailed regulatory, e.g., FDA, specifications. In one embodiment, the approved indications and usages include instructions on how to use the ergoline derivatives of the invention to prevent or treat a disorder associated with cephalic pain, e.g., a cluster headache. In another embodiment, the approved indications and usages include instructions on how to use ergoline derivatives of the invention in combination with one or more other compounds, e.g., one or more compounds described herein, e.g., opioid receptor antagonists, to treat or prevent a disorder associated with cephalic pain, e.g., a cluster headache.

The ergoline derivatives of the invention and the additional preventative or therapeutic compounds described herein can be administered according to any technique deemed suitable by one of skill in the art. For example, the ergoline derivatives or various compositions thereof of the invention, can be administered by any of the following means: (a) enterally, e.g., orally (by mouth), rectally (e.g., in the form of a suppository or an enema), by feeding tube (e.g., gastric feeding tube, duodenal feeding tube, gastrostromy); (b) parenterally, e.g., subcutaneously, intravenously, intramuscularly, intradermally (into the skin itself), transdermally (diffusion through skin, e.g., intact skin), intra-arterially, intra-peritoneally, intracardiac (into the heart) administration, intraosseous (into the bone marrow) administration, intrathecally (into the spinal canal), transmucosally (diffusion through a mucous membrane, e.g., insufflation (snorting), nasally, e.g., intranasally), sublingually (under the tongue), buccally (through the cheek), vaginally, by inhalation (e.g., pulmonary administration); (c) topically; (d) epidurally (injection or infusion into the epidural space); and (e) intravitreally. If the ergoline derivative or the additional preventative or therapeutic compound described herein is to be used acutely, e.g., to abort an attack of a disorder associated with cephalic pain, methods or routes of administration which result in rapid onset of action are preferred. These methods or routes of administration include administration by parenteral (e.g., subcutaneous (e.g., subcutaneous periorbital administration), intramuscular or intravenous administration) or pulmonary (e.g., by inhalation) or transmucosal (e.g., through a nasal spray) routes.

The ergoline derivatives of the invention, pharmaceutically acceptable salts thereof, and/or pharmaceutical compositions thereof can be used to treat disorders or conditions associated with cephalic pain. In some embodiments, the methods of the invention include methods for treating a disorder associated with cephalic pain by administering a therapeutically effective amount of the ergoline derivative, alone or in combination with the additional preventative and/or therapeutic compounds described herein, to a subject in need of such treatment.

As used herein, the terms "treating" or "treatment" of any disease or disorder refers, in one embodiment, to ameliorating the disease or disorder (i.e., arresting or reducing the development of the disease or at least one of the clinical symptoms thereof) that exists in a subject. In another embodiment, "treating" or "treatment" refers to ameliorating at least one physical parameter, which may or may not be indiscernible by the subject. In yet another embodiment, "treating or treatment" refers to modulating the disease, either physically (e.g., stabilization of a discernable symptom) or physiologically (e.g., stabilization of a physical parameter) or both. Subjects who suffer from CH, for example, often experience one or more of the following symptoms: severe, unilateral pain attacks localized to orbital, supraorbital, temporal or combinations of these sites and accompanied by, ipsilateral to the site of pain, one or more of: lacrimation or conjunctival injection, rhinorrhea or nasal congestion, cranial and/or facial sweating, miosis and/or ptosis, edema of the eyelid or orofacial tissues (including the gingival and palate), facial flushing or pallor, swelling around the eye and orofacial tissues (including the mouth), thermography determined "cold spot" at the site of pain (usually supraorbital). These subjects can also suffer from one or more of the following: bradycardia, vertigo and ataxia, syncope, hypertension, increased gastrointestinal acid, hyperalgesia or allodynia at the site of pain, posturing, twitching and paresthesia of body parts. Subjects who suffer from migraines, for example, often experience one or more of the following symptoms: aura (visual, sensory, and/or motor), photophobia, phonophobia, osmophobia, nausea, vomiting, vertigo, and paresthesias. Thus, treating a subject according to the methods of the present invention can include alleviating or reducing one, two, three or more of the above-listed symptoms.

As used herein, a disorder or condition associated with cephalic pain is a disorder or condition which has as one of its symptoms cephalic/head pain (e.g., headache). Examples of such disorders or conditions include trigeminal autonomic cephalalgias such as episodic and chronic cluster headache (CH), episodic and chronic paroxysmal hemicrania (PH), and short-lasting unilateral neuralgiform headache attacks with conjunctival injection and tearing (SUNCT). Other examples of disorders or conditions which can be treated according to the present invention include vascular headaches (e.g., migraine headaches), tension headaches, headaches associated with the use of a substance (e.g., triptans such as sumatriptan, benzodiazepines such as alprazolam, analgesics such as ibuprofen, ergots such as ergotamine, opioids such as morphine, recreational drugs such as caffeine, nicotine, alcohol, and hormone replacement therapy containing, for example, estrogen) or its withdrawal. Yet additional examples of disorders or conditions associated with cephalic pain include miscellaneous headache unassociated with a structural lesion, headache associated with a nonvascular intracranial disorder, headache associated with a non-cephalic infection, headache associated with a metabolic disorder, headache associated with a disorder of the cranium, neck, eyes, nose, sinuses, teeth, mouth, or other facial or cranial structure, nerve trunk pain and deafferentiation pain.

As used herein, an "effective amount" or "therapeutically effective amount" means an amount of an ergoline derivative or another therapeutic or preventative compound, e.g., the short and long acting compounds, described herein, that when administered to a subject for preventing or treating a disease or disorder, is sufficient to effect such prevention or treatment of the disease or disorder. An effective amount can vary depending on, among other things, the ergoline derivative used, the disease and its severity and the age, weight, etc. of the subject to be treated. The dosage and frequency of administration of the ergoline derivatives or therapeutic or preventative compound described herein, can be determined by one skilled in the art. The amount of such compound that will be effective in the treatment of a disorder or condition will vary with the nature and severity of the disorder or condition, and the route by which the active ingredient is administered. The frequency and dosage will also vary according to factors specific for each patient depending on the severity of the disorder or condition, the route of administration, as well as age, body weight, response, and the past medical history of the patient. Effective doses can be extrapolated from dose-response curves derived from in vitro or animal model test systems.

In some embodiments, the dose comprises the ergoline derivative in an amount:
between about 25 µg and about 10 mg, preferably
between about any of: 25, 30, 35, 40, 45, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, and 1000 µg (i.e., 1 mg); and any of: about 1000, 1250, 1500, 1750, 2000, 2250, 2500, 2750, 3000, 3250, 3500, 3750, 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750 µg, and 10 mg; and more preferably
between about 50 µg and about 2000 µg.

As used herein, the term "about" refers to a value that is no more than 20% above or below the value being modified by the term. For example, the term "about 4 mg" means a range of from 3.2 mg to 4.8 mg.

In certain embodiments, the ergoline derivative is administered at a dosage described herein at least once a day, at least once every other day, at least once every third day, at least once every fourth day, or at least once every fifth day or more days to treat or prevent a disorder associated with cephalic pain. The ergoline derivative can thus be administered at a dose described herein at least once a day, at least once every other day, at least once every third day, at least once every fourth day, or at least once every fifth day or more for at least one day, two days, three days, four days, five days or more or at least once a day, at least once every other day, at least once every third day, at least once every fourth day, or at least once every fifth day or more at least three times. In one embodiment, the ergoline derivative is administered at least once a day for at least three days. In another embodiment, the ergoline derivative is administered at least once every fifth day three times. In yet other embodiments, the subject to whom the ergoline derivative is administered has not received a headache medication (e.g., has been weaned off any headache medication that he or she was already taking) for at least one day, two days, three days, four days, or five days or more prior to administration of the ergoline derivative.

In other embodiments, the dose of the ergoline derivative administered to the subject is decreased over the course of repeated administrations. In yet other embodiments, the dose of the ergoline derivative administered to a subject is increased over the course of repeated administrations.

In certain embodiments, the methods and formulations can be practiced as a single, one time dose or chronically. By chronic it is meant that the methods and compositions of the invention are practiced more than once to a given subject or individual. For example, chronic administration can be multiple doses of a pharmaceutical composition administered to a subject, on a weekly basis, a biweekly basis, monthly basis, or more or less frequently, as will be apparent to those of skill in the art. Chronic administration can continue for weeks, months, or years if appropriate according to the judgment of the practitioner of skill in the art. Furthermore, if certain doses, in the judgment of the practitioner of skill in the art, show tolerability profiles which may not be acceptable, the practitioner can reduce the dose to reduce such profiles.

An effective amount of an ergoline derivative described herein will provide therapeutic benefit without causing substantial toxicity. Toxicity of an ergoline derivative can be determined by standard pharmaceutical procedures in cell cultures or experimental animals, for example, by determining the LD50 (the dose lethal to 50% of the population) or the LD100 (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1996, In: The Pharmacological Basis of Therapeutics, 9th ed., Chapter 2, p. 29, Elliot M. Ross)

As used herein, "subject" refers to an animal such as a mammal, including but not limited to, a primate (e.g., human), cow, sheep, goat, horse, dog, cat, rabbit, rat, mouse and the like. In preferred embodiments, the subject is human. In other preferred embodiments, the subject is a human who is in need of treatment or preventative therapy according to the present invention, e.g., a human who has or who suffers from, or is susceptible to, a disorder associated with cephalic pain. In another embodiment, the subject is a human who has not received a headache medication for a certain period of time (e.g., at least one day, at least two days, at least three days, at least four days, at least five days or more) prior to administration of the ergoline derivative. In yet other embodiments, the subject is a human who has received a headache medication prior to administration of the ergoline derivative but in amounts less than that subject would normally take absent the administration of the ergoline derivative.

For acute treatment of disorders associated with cephalic pain, the ergoline derivatives can be administered to a subject in need thereof in combination with a second compound or agent which acutely relieves at least one symptom of such disorder. Examples of such compounds or agents which acutely relieve at least one symptom of a disorder associated with cephalic pain include gases, e.g., oxygen, serotonin receptor agonists (e.g., triptans such as sumatriptan, eletriptan, rizatriptan, frovatriptan, almotriptan, zolmitriptan, and naratriptan), ergot derivatives (e.g., dihydroergotamine, and ergotamine tartrate), hormones (e.g., corticosteroids (e.g., prednisone, cortisol), testosterone, growth hormone, luteinizing hormone, somatostatin, and prolactin), and local anesthetics (e.g., amino ester local anesthetics (e.g., benzocaine, chloroprocaine, cocaine, procaine, and tetracaine/amethocaine), amino amide local anesthetics (e.g., bupivacaine levobupiva, lidocaine/lignocaine, mepivacaine, prilocalne, ropivacaine, articaine, trimecaine, and combinations thereof (e.g., lidocaine and prilocalne). Moreover, more than one of these second compounds or agents can be administered to the subject with the ergoline derivative in the methods of the invention. Table I below provides a sample list of these compounds or agents together with examples of dosages and routes of administration that can be used in combination with the ergoline derivatives described herein to treat disorders described herein, e.g., especially to acutely treat a disorder described herein.

In one embodiment, the methods of the invention include methods of treating disorders associated with cephalic pain, e.g., cluster headaches, by administering an ergoline derivative described herein, e.g., a substantially pure form of an ergoline derivative described herein, and by administering, as needed to treat acute attacks of cephalic pain during the period in which the ergoline derivative is being administered, a second compound or agent (e.g., one or more of those agents listed in Table I) which acutely relieves at least one symptom of such disorder. An example of this method of treatment is when a subject is being treated with three doses of LSA, e.g., a substantially pure form of LSA, or 2-bromo-LSD, e.g., a substantially pure form of 2-bromo-LSD, spaced five days apart and to treat cephalic pain attacks that occur during this treatment period, either inhaled oxygen or intranasal lidocaine is also administered.

In another embodiment, the methods of the invention include methods of treating disorders associated with cephalic pain, e.g., cluster headaches, by administering an ergoline derivative described herein, e.g., a substantially pure form of an ergoline derivative described herein, and by administering, after treatment with the ergoline derivative has ended, a second compound or agent (e.g., one or more of those agents listed in Table I) which acutely relieves at least one symptom of such disorder. In this method, the second compound or agent is used to treat "breakthrough" attacks that can occur following a complete course of treatment with an ergoline derivative.

TABLE I

| Compound Class | Specific Compound | Dose | Route of Administration |
|---|---|---|---|
| Gas | Oxygen (e.g., 100% oxygen) | 7-12 L/minute for 15-30 minutes | Inhalation (e.g. by facial mask) |
| Serotonin receptor agonist | Sumatriptan | (a) 6 mg; or (b) 20 mg | (a) Subcutanous injection; or (b) nasal spray |
|  | Zolmitriptan | 5 mg or 10 mg | Nasal spray |
| Ergot derivative | Dihydroergotamine | 1 mg (2 sprays each nostril)-may repeat once, if needed | Nasal spray |
|  | Dihydroergotamine | 0.5-1.0 mg | Intravenous or intramuscular injection |
|  | Ergotamine | 1-2 mg (max. 6 mg/day) | Oral tablets |
| Local anesthetic | Lidocaine (e.g., 4-6%) | 4 sprays (e.g., ipsilaterally) | Nasal spray |

In some embodiments, the methods of the invention include methods for treating a disorder associated with cephalic pain by administering a therapeutically effective amount of the ergoline derivative in combination with a therapeutically effective amount of an opioid receptor antagonist to a subject in need of such treatment.

As used herein, the term "opioid receptor antagonist" refers to a compound which binds to an opioid receptor but which does not elicit a biological response by binding to the receptor. Opioid receptor antagonists can bind to one or more (and in any combination) of the opioid receptors (e.g., delta, kappa, or mu and their subclasses). Examples of opioid receptor antagonists that can be used according to the methods of the invention include naloxone (e.g., naloxone hydrochloride) and naltrexone (e.g., naltrexone hydrochloride). In some embodiments, the opioid receptor antagonist is administered to the subject prior to (e.g., immediately prior to, e.g, within minutes or hours of) or concurrently with administration of the ergoline derivatives described herein. In some embodiments, the opioid receptor antagonist is administered to a subject after (e.g., immediately after, e.g., within minutes or hours after) the ergoline derivatives described herein. In other embodiments, the use of the opioid receptor antagonist increases the potency of the ergoline derivative and can decrease waiting periods between doses of the ergoline derivative. For example, instead of taking 0.5 mg of LSA every five days for three doses, the subject will be able to take 0.1 mg of LSA combined with 50 mg or less of naltrexone every day for three days with the same effect. Thus, use of an opioid receptor antagonist in combination with an ergoline derivative described herein to treat or prevent the disorders described herein allows the use of a lesser dose of the ergoline derivative to achieve the same result.

In one embodiment, the opioid receptor antagonist is naloxone which can be administered, for example, either transmucosally (e.g., sublingually, e.g., in tablet form), intravenously, subcutaneously, or orally. For intravenous administration, naloxone can be administered at a dose of between about 0.1 mg and about 2 mg every 2 to 3 minutes as needed. In another embodiment, the opioid receptor antagonist is naltrexone hydrochloride which can be administered, for example, orally (in tablet form) at a dose of between about 5 mg and about 125 mg, preferably of between about 25 mg and 100 mg, and most preferably at about 50 mg.

The invention is also directed to methods for preventing a disorder associated with cephalic pain in a subject in need thereof which comprise administering to the subject, during a period in which the subject is not suffering from cephalic pain, a therapeutically effective amount of an ergoline derivative, alone or in combination with another preventative or therapeutic compound such as a mood stabilizer, e.g., lithium, a hormone, e.g., melatonin, a calcium channel blocker, a hormone, an anticonvulsant agent, an opioid receptor antagonist, a vanilloid, and a sedative (e.g., prochlorperzine). For example, lithium can be administered orally either twice a day or dialing in an extended release formulation. Melatonin can be administered orally daily. Calcium channel blockers can be administered orally up to three times a day. Vanilloids, e.g., capsaicin, can be administered by placing a cotton swab in the nostril during an acute cephalic pain attack. Hormones such as dihydroepiandrosterone (DHEA) can be administered in the form of a nasal spray during an acute cephalic pain attack. Sedatives can also be administered during an acute attack of cephalic pain.

As used herein, "preventing" or "prevention" of any disease or disorder refers to a reduction in the risk of acquiring a disease, disorder, or condition (i.e., causing at least one of the clinical symptoms of the disease or disorder not to develop in a subject who may be predisposed or susceptible to the disease or disorder or who already suffers from the disease or disorder but who is in a remission period). In one embodiment, the subject does not yet experience or display symptoms of the disease or disorder. In another embodiment, the subject has or suffers from a disorder associated with cephalic pain but is not, at the time of administration of the ergoline derivative, alone or in combination with another compound described herein, experiencing cephalic pain, e.g., the subject is in a remission period (i.e., a period during which the symptoms of the disease, disorder, or condition have abated or subsided) from the cephalic pain. Preferably, the terms preventing and prevention refer to the use of a compound or composition in a subject who is in remission from the disorder and, when the subject is treated according to the prevention methods described herein, the remission period is extended. Table II below provides a sample list of compounds or agents together with examples of dosages and routes of administration that can be used in combination with the ergoline derivatives described herein to prevent disorders described herein.

TABLE II

| Compound Class | Specific Compound | Dose | Route of Administration |
|---|---|---|---|
| Calcium channel blocker | Verapamil | 360-720 mg/d | oral |
| Corticosteroid | Prednisone | 60-80 mg/d | oral |
| Mood stabilizer | Lithium | 300-1200 mg/d | oral |
| Anti-convulsant | Valproic acid | 1000-1250 mg/d | oral |
|  | Topiramate | 50-200 mg/d | oral |
|  | Gabapentin | 300-900 mg/d | oral |
| Hormone | Melatonin | 3-10 mg/nightly | oral |
| Vanilloid | Capsaicin (0.025% cream) | Place via cotton swab in nostril for 7 d | intranasal |

In other embodiments, the methods of the invention include administering both an ergoline derivative, e.g., LSA, e.g., LSA in substantially pure form, e.g., 2-bromo-LSD, e.g., a substantially pure form of 2-bromo-LSD, with a leukotriene antagonist drug to a treat or prevent a disorder described herein. In other embodiments, the methods of the invention include administering both the ergoline derivative, e.g., LSA, e.g., LSA in substantially pure form, e.g., 2-bromo-LSD, e.g., a substantially pure form of 2-bromo-LSD, with a non-steroidal anti-inflammatory drug (NSAID), e.g., naproxen, flurbiprofen, ketoprofen, oxaprozin, etodolac, indomethacin, ketorolac, nabumetone, mefanamic acid, and piroxican, a COX-2 inhibitor (e.g., celecoxib, rofecoxib, meloxicam) to a treat or prevent a disorder described herein. A preferred COX-2 inhibitor is celecoxib which can be used at a dose of between 50 and 500 mg. In one embodiment, the ergoline derivative, e.g., LSA, 2-bromo-LSD, and the NSAID are used together with a serotonin receptor agonist to treat or prevent a disorder described herein. In other embodiments, the methods of the invention include administering both the ergoline derivative, e.g., LSA, 2-bromo-LSD, and an antipsychotic drug to treat or prevent a disorder described herein. In yet other embodiments, the methods of the invention include administering both the ergoline derivative, e.g., LSA, 2-bromo-LSD, and a B vitamin, e.g., riboflavin and/or niacin, to a treat or prevent a disorder described herein.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating a disorder associated with cephalic pain wherein said disorder is trigeminal autonomic cephalagia, comprising enterally, sublingually or parenterally administering to a subject in need of such treatment a therapeutically effective amount of a substantially pure form of lysergic acid amide (LSA) or bromo-lysergic acid diethylamide (bromo-LSD) present in a composition in an amount of between about 50 µg and about 5000 µg.

2. The method of claim 1, wherein the trigeminal autonomic cephalalgia is selected from the group consisting of episodic and chronic cluster headache (CH), episodic and chronic paroxysmal hemicrania (PH), and short-lasting unilateral neuralgiform headache attacks with conjunctival injection and tearing (SUNCT).

3. The method of claim 2, wherein the trigeminal autonomic cephalalgia is episodic or chronic CH.

4. The method of claim 1, further comprising administering to the subject a second compound which acutely relieves at least one symptom of the disorder associated with cephalic pain.

5. The method of claim 4, wherein the second compound is selected from the group consisting of oxygen, a serotonin receptor agonist, an ergot derivative, a hormone, and a local anesthetic.

6. The method of claim 1, further comprising administering a second compound selected from the group consisting of lithium, melatonin, a calcium channel blocker, a hormone, an anticonvulsant agent, an opioid receptor antagonist and a sedative.

7. The method of claim 1, wherein the LSA or bromo-LSD is in an amount of between about 100 µg and about 2000 µg in a pharmaceutically acceptable carrier.

8. The method of claim 1, wherein the LSA or bromo-LSD is in an amount of between about 100 µg and about 1000 µg in a pharmaceutically acceptable carrier.

9. The method of claim 1, wherein said administering is through parenteral administration.

10. The method of claim 1, wherein said administering is through enteral administration.

11. The method of claim 9, wherein said parenteral administration is subcutaneous administration, intravenous administration, intramuscular administration, and transmucosal administration.

* * * * *